(12) United States Patent
Nakagawa et al.

(10) Patent No.: US 10,454,038 B2
(45) Date of Patent: Oct. 22, 2019

(54) DELAYED-FLUORESCENCE MATERIAL AND ORGANIC ELECTROLUMINESCENCE ELEMENT USING SAME

(75) Inventors: Tetsuya Nakagawa, Fukuoka (JP); Chihaya Adachi, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 396 days.

(21) Appl. No.: 14/233,012

(22) PCT Filed: Jul. 13, 2012

(86) PCT No.: PCT/JP2012/067970
§ 371 (c)(1),
(2), (4) Date: Jan. 15, 2014

(87) PCT Pub. No.: WO2013/011955
PCT Pub. Date: Jan. 24, 2013

(65) Prior Publication Data
US 2014/0138669 A1 May 22, 2014

(30) Foreign Application Priority Data
Jul. 15, 2011 (JP) .................................. 2011-157032

(51) Int. Cl.
*H01L 51/00* (2006.01)
*C07C 255/58* (2006.01)
(Continued)

(52) U.S. Cl.
CPC ........ *H01L 51/0056* (2013.01); *C07C 255/58* (2013.01); *C07D 209/86* (2013.01);
(Continued)

(58) Field of Classification Search
CPC .... H05B 33/14; C07C 255/58; C07D 519/00; C07D 209/86; C09K 11/06;
(Continued)

(56) References Cited

U.S. PATENT DOCUMENTS 7,701,131 B2 4/2010 Gerhard et al.
7,862,904 B2 1/2011 Vestweber et al.
(Continued)

FOREIGN PATENT DOCUMENTS

JP 06043963 B2 8/1994
JP 07278537 A 10/1995
(Continued)

OTHER PUBLICATIONS

Chien, Yuh-Yih et al "Syntheses and spectroscopic studies of spirobifluorene-bridged bipolarsystems; photoinduced electron transfer reactionsf" Chem. Commun. 23:2874-2875 (Nov. 2002).
(Continued)

*Primary Examiner* — Alexander C Kollias
(74) *Attorney, Agent, or Firm* — Browdy and Neimark, P.L.L.C.

(57) ABSTRACT

A delayed fluorescence material comprising a compound represented by the general formula below. At least one of $R^1$ to $R^8$ represent an electron-donating group and the others represent a hydrogen atom; at least one of $R^9$ to $R^{16}$ represent an electron-withdrawing group and the others represent a hydrogen atom.

(Continued)

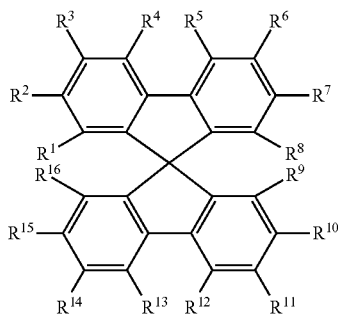

17 Claims, 7 Drawing Sheets

(51) Int. Cl.
C07D 519/00 (2006.01)
C07D 209/86 (2006.01)
C09K 11/06 (2006.01)
H05B 33/14 (2006.01)
H01L 51/50 (2006.01)

(52) U.S. Cl.
CPC ............ *C07D 519/00* (2013.01); *C09K 11/06* (2013.01); *H01L 51/5012* (2013.01); *H05B 33/14* (2013.01); *C09K 2211/1011* (2013.01); *H01L 51/0072* (2013.01)

(58) Field of Classification Search
CPC ......... C09K 2211/1011; H01L 51/5012; H01L 51/0056; H01L 51/0072
See application file for complete search history.

(56) References Cited

U.S. PATENT DOCUMENTS

| 2006/0068221 | A1* | 3/2006 | Saitoh .................... C09K 11/06 428/690 |
| 2009/0167166 | A1 | 7/2009 | Bach et al. |
| 2010/0019658 | A1 | 1/2010 | Lin et al. |
| 2011/0028723 | A1* | 2/2011 | Li ........................ C07F 15/0086 546/4 |
| 2012/0126179 | A1* | 5/2012 | Parham ................... C07C 13/72 252/500 |

FOREIGN PATENT DOCUMENTS

| JP | 2001509888 A | 7/2001 | |
| JP | 2001307879 A | 11/2001 | |
| JP | 2002121547 A | 4/2002 | |
| JP | 2003149152 A | 5/2003 | |
| JP | 2005-174736 A | 6/2005 | |
| JP | 2006256982 A | 9/2006 | |
| JP | 2006528836 A | 12/2006 | |
| JP | 2008096360 A | 4/2008 | |
| JP | 2008281467 A | 11/2008 | |
| JP | 2009203176 A | 9/2009 | |
| JP | 2009538841 A | 11/2009 | |
| JP | 201027681 A | 2/2010 | |
| JP | 2013253121 A | 12/2013 | |
| WO | 9826709 A1 | 6/1998 | |
| WO | WO 2011006574 | * 1/2011 | ............. C09K 11/06 |

OTHER PUBLICATIONS

Wong, Ken-Tsung et al "Synthesis, Structures, and Photoinduced Electron Transfer Reaction in the 9,9'—Spirobifluorene-Bridged Bipolar Systems" The Journal of Organic Chemistry. 71(2): 456-465 (Dec. 2005).
Nakagawa, Tetsuya et al "Electroluminescence based on thermally activated delayed fluorescence generated by a spirohifluorene donor-acceptor structuret" Chem. Commun. 48(77): 9580-9582 (Apr. 2012).
Milian-Medina, Begona et al "Computational design of low singlet-triplet gap all-organic molecules for OLED application" Organic Electronics 13(6):985-991 (Feb. 2012).
European Search Report dated May 19, 2015 in corresponding European appl. No. 12814370.8.
Office Action dated May 20, 2014 issued in the corresponding Japanese Patent application 2012092586.
Chinese Office Action dated Jul. 27, 2015 issued in the corresponding Chinese Patent Application No. 201280035233.4.
Japanese Office Action dated Sep. 8, 2015 issued in the corresponding Japanese patent application No. 2013-524707.
International preliminary report on patentability in connection with corresponding PCT/JP2012/067970 dated Jul. 13, 2012.
Hung et al., Physical Chemistry Chemical Physics, 10, pp. 5822-5825 (Aug. 13, 2008).
Ku et al., Chemistry—An Asian Journal, pp. 133-142 (Oct. 13, 2011).
Endo et al., Efficient up-conversion of triplet excitons into a singlet state and its application for organic light emitting diodes, Appl. Phys. Lett., 98:083302-083302-3(2011).
Parac et al., A TDDFT study of the lowest excitation energies of polycyclic aromatic hydrocarbons, Chemical Physics, 292:11-21 (2003).
Nijegorodov et al., Evolution of absorption, fluorescence, laser and chemical properties in the series of compounds perylene, benzo(ghi)perylene and coronene, Spectrochimica Acta Part A, 57:2673-2685 (2001).
Benniston et al., Opening a Spiropyran Ring by Way of an Exciplex Intermediate, J. Org. Chem., 72:888-897 (2007).

* cited by examiner

DELAYED-FLUORESCENCE MATERIAL AND ORGANIC ELECTROLUMINESCENCE ELEMENT USING SAME

TECHNICAL FIELD

The present invention relates to a delayed fluorescence material having a high emission efficiency, and to an organic electroluminescence element (organic EL element) using the material in the light-emitting layer therein.

BACKGROUND ART

A lot of studies for increasing the emission efficiency of organic electroluminescence elements are being made. In particular, various kinds of efforts have been made to increase the emission efficiency by newly developing and combining an electron transport material, a hole transport material, a light-emitting materials and others that constitute an organic electroluminescence element. Among them, there are seen some studies relating to an organic electroluminescence element that utilizes a spirobifluorene structure-having compound, for which some proposals have heretofore been made.

For example, PTL 1 describes a phosphorescent organic electroluminescence element that uses a spirobifluorene structure-having compound in the hole blocking layer therein. PTL 2 describes an organic electroluminescence element that uses a compound having a spirobifluorene structure with two carbazole groups bonding thereto, as a host material in the light-emitting layer therein. Further, PTL 3 describes an organic electroluminescence element that uses a compound having a spirobifluorene structure substituted with a phenylvinyl group or a phenyl group, as a host material in the light-emitting layer therein. PTL 4 describes an organic electroluminescence element in which the light-emitting layer is formed of only a compound that has a spirobifluorene structure substituted with a biphenyl group. PTL 5 describes an organic electroluminescence element in which the light-emitting layer is formed of only a benzene or naphthalene compound substituted with from 1 to 3 spirobifluorene rings. PTL 6 describes an organic electroluminescence element in which the light-emitting layer is formed of only a benzene compound substituted with from 3 to 6 spirobifluorene rings.

CITATION LIST

Patent Literature

PTL 1: JP-T 2006-528836
PTL 2: JP-A 2010-27681
PTL 3: JP-A 2001-307879
PTL 4: JP-A 7-278537
PTL 5: JP-A 2002-121547
PTL 6: JP-A 2006-256982

SUMMARY OF INVENTION

Technical Problem

As in the above, various investigations of spirobifluorene structure-having compounds have heretofore been made, and some proposals relating to application of those compounds to organic electroluminescence elements have been made. However, it could not be said that comprehensive studies relating to all such spirobifluorene structure-having compounds could have been achieved thoroughly. In particular, regarding use of a spirobifluorene structure-having compound as a light-emitting material in an organic electroluminescence element, usefulness of only a part of such compounds has heretofore been confirmed. In addition, any definite relationship between the chemical structure of a spirobifluorene structure-having compound and the usefulness of the compound as a light-emitting material could not be found out as yet, and the situation is that it is difficult to anticipate the usefulness of the compound as a light-emitting material based on the chemical structure thereof. Further, synthesis of a spirobifluorene structure-having compound is not always easy, and therefore it is also difficult to provide the compound itself. Taking these problems into consideration, the present inventors synthesized various spirobifluorene structure-having compounds and advanced the investigation for evaluating in detail the usefulness of those compounds as a light-emitting material in organic electroluminescence elements. In addition, the inventors made assiduous studies for the purpose of leading out a general formula of compounds useful as a light-emitting material and generalizing the constitution of an organic electroluminescence element having a high emission efficiency.

Solution to Problem

For attaining the above-mentioned objects, the present inventors made assiduous studies and, as a result, have found that specific compounds having a spirobifluorene structure have an excellent property as a delayed fluorescence material for organic electroluminescence elements. Based on this finding, the present inventors have provided the present invention described hereinunder, as a solution to the above problems.

[1] A delayed fluorescence material comprising a compound represented by the following general formula (1)

[Chem. 1]

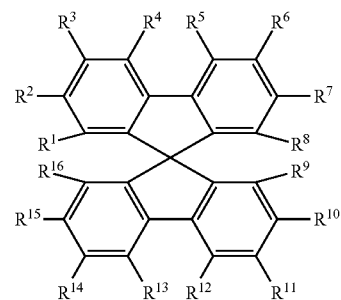

General Formula (1)

In the general formula (1), $R^1$, $R^2$, $R^3$, $R^4$, $R^5$, $R^6$, $R^7$ and $R^8$ each independently represent a hydrogen atom or an electron-donating group, and at least one of these is an electron-donating group. $R^9$, $R^{10}$, $R^{11}$, $R^{12}$, $R^{13}$, $R^{14}$, $R^{15}$ and $R^{16}$ each independently represent a hydrogen atom or an electron-withdrawing group, and at least one of these is an electron-withdrawing group.

[2] The delayed fluorescence material according to [1], wherein at least two of $R^1$, $R^2$, $R^3$, $R^4$, $R^5$, $R^6$, $R^7$ and $R^8$ in the general formula (1) each are an electron-donating group.

[3] The delayed fluorescence material according to [1], wherein, in the general formula (1), at least one of $R^1$, $R^2$, $R^3$ and $R^4$ is an electron-donating group, and at least one of $R^5$, $R^6$, $R^7$ and $R^8$ is an electron-donating group.

[4] The delayed fluorescence material according to [1], wherein, in the general formula (1), at least one of $R^2$ and $R^3$ is an electron-donating group, and at least one of $R^6$ and $R^7$ is an electron-donating group.

[5] The delayed fluorescence material according to [1], wherein, in the general formula (1), $R^2$ or $R^3$ is an electron-donating group and $R^6$ or $R^7$ is an electron-donating group.

[6] The delayed fluorescence material according to any one of [1] to [5], wherein at least one of $R^1$, $R^2$, $R^3$, $R^4$, $R^5$, $R^6$, $R^7$ and $R^8$ is an electron-donating group that contains a structure represented by any of the following general formulae (2) to (4):

[Chem. 2]

General Formula (2)

General Formula (3)

General Formula (4)

In the general formula (2), $Z^1$ represents a nitrogen atom, an oxygen atom, a sulfur atom or a silicon atom, and may form, each independently at $A^1$ and $A^2$, an aromatic ring, a heteroaromatic ring, an aliphatic ring or a nonaromatic hetero ring. In the general formula (3), $R^{20}$ represents a hydrogen atom, an aryl group or an atomic group necessary for forming the ring structure represented by $A^4$, and may form, each independently as $A^3$ and $A^4$, a heteroaromatic ring or a nonaromatic hetero ring. In the general formula (4), $Z^1$, $Z^2$, $Z^3$ and $Z^4$ each independently represent an oxygen atom or a sulfur atom.

[7] The delayed fluorescence material according to any one of [1] to [5], wherein at least one of $R^1$, $R^2$, $R^3$, $R^4$, $R^5$, $R^6$, $R^7$ and $R^8$ is an electron-donating group that contains a structure of any of the following D1 to D10:

[Chem. 3]

D1

D2

D3

D4

D5

D6

D7

D8

D9

D10

[8] The delayed fluorescence material according to [7], wherein at least one of $R^1$, $R^2$, $R^3$, $R^4$, $R^5$, $R^6$, $R^7$ and $R^8$ is an electron-donating group that contains a structure represented by the above D3 or D9.

[9] The delayed fluorescence material according to any one of [1] to [8], wherein at least two of $R^9$, $R^{10}$, $R^{11}$, $R^{12}$, $R^{13}$, $R^{14}$, $R^{15}$ and $R^{16}$ in the general formula (1) each are an electron-withdrawing group.

[10] The delayed fluorescence material according to any one of [1] to [8], wherein, in the general formula (1), at least one of $R^9$, $R^{10}$, $R^{11}$ and $R^{12}$ is an electron-withdrawing group, and at least one of $R^{13}$, $R^{14}$, $R^{15}$ and $R^{16}$ is an electron-withdrawing group.

[11] The delayed fluorescence material according to any one of [1] to [8], wherein, in the general formula (1), $R^{10}$ or $R^{11}$ is an electron-withdrawing group, and $R^{14}$ or $R^{15}$ is an electron-withdrawing group.

[12] The delayed fluorescence material according to any one of [1] to [8], wherein, in the general formula (1), $R^{10}$ or $R^{11}$ is a cyano group, and $R^{14}$ or $R^{15}$ is a cyano group.

[13] An organic electroluminescence element having an anode, a cathode, and at least one organic layer containing a light-emitting layer between the anode and the cathode, wherein the light-emitting layer contains the delayed fluorescence material of any one of [1] to [12].

[14] A compound represented by the following general formula (1'):

[Chem. 4]

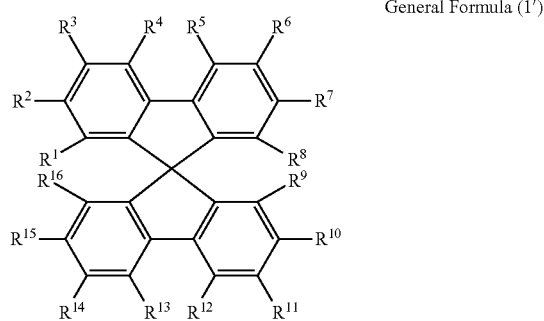

General Formula (1')

In the general formula (1') $R^1$, $R^2$, $R^3$, $R^4$, $R^5$, $R^6$, $R^7$ and $R^8$ each independently represent a hydrogen atom or an electron-donating group, and at least one of these is an electron-donating group that contains a structure represented by any of the above-mentioned general formulae (2) to (4). $R^9$, $R^{10}$, $R^{11}$, $R^{12}$, $R^{13}$, $R^{14}$, $R^{15}$ and $R^{16}$ each independently represent a hydrogen atom or an electron-withdrawing group, and at least one of these is an electron-withdrawing group.

[15] The compound according to [14], wherein at least one of $R^1$, $R^2$, $R^3$, $R^4$, $R^5$, $R^6 R^7$ and $R^8$ is an electron-donating group that contains a structure represented by any of the above D1 to D8.

[16] The compound according to [15], wherein at least one of $R^1$, $R^2$, $R^3$, $R^4$, $R^5$, $R^6$, $R^7$ and $R^8$ is an electron-donating group that contains a structure represented by the above D9.

Advantageous Effects of Invention

The delayed fluorescence material of the invention is a first-ever delayed fluorescence material having a spirobifluorene structure. Use of the delayed fluorescence material of the invention is used as a light-emitting material provides an organic electroluminescence element having a high emission efficiency.

DESCRIPTION OF EMBODIMENTS

Figure 1:
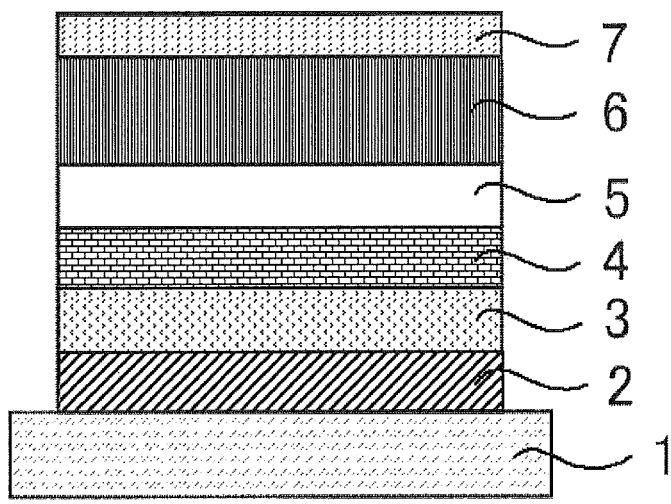
FIG. 1 This is a schematic cross-sectional view showing a layer configuration of the organic electroluminescence element of Examples.

The contents of the invention are described in detail hereinunder. The description of the constitutive elements of the invention given hereinunder is for some typical embodiments and specific examples of the invention; however, the invention should not be limited to such embodiments and specific examples. In this description, the numerical range expressed by the wording "a number to another number" means the range that falls between the former number indicating the lower limit of the range and the latter number indicating the upper limit thereof.

[Compound Represented by General Formula (1)]

The delayed fluorescence material of the invention contains a compound represented by the following general formula (1). The compound represented by the general formula (1) is first described.

[Chem. 5]

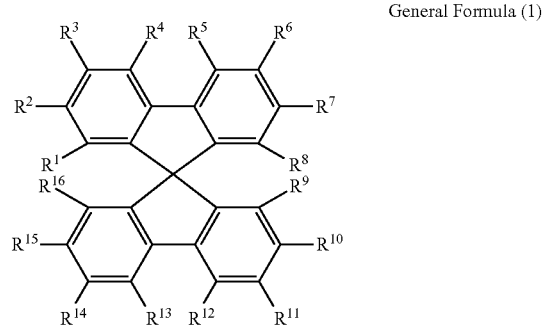

General Formula (1)

In the general formula (1) $R^1$, $R^2$, $R^3$, $R^4$, $R^5$, $R^6$, $R^7$ and $R^8$ each independently represent a hydrogen atom or an electron-donating group. However, at least one of these is an electron-donating group. When two or more of these are electron-donating groups, those two or more electron-donating groups may be the same or different. Preferably, they are the same. Of $R^1$, $R^2$, $R^3$, $R^4$, $R^5$, $R^6$, $R^7$ and $R^8$, preferably, any one or more of $R^2$, $R^3$, $R^4$, $R^5$, $R^6$ and $R^7$, more preferably two or more of these are electron-donating groups. Preferably, one or more of $R^2$, $R^3$, $R^6$ and $R^7$, more preferably two or more of these are electron-donating groups. Even more preferably, one or more of $R^2$, $R^3$, $R^6$ and $R^7$, more preferably two or more of these are electron-donating groups. In case where two or more are electron-donating groups, preferably, one of $R^2$ and $R^3$, and one of $R^6$ and $R^7$ are electron-donating groups.

The electron-donating group represented by $R^1$, $R^2$, $R^3 R^4$, $R^5$, $R^6$, $R^7$ and $R^8$ is a group which, when bonding to the spirobifluorene ring, exhibits a property of donating an electron to the ring. The electron-donating group may be any of an aromatic group, a heteroaromatic group or an aliphatic group, or may be a composite group formed of two or more of these groups. Examples of the electron-donating group include an alkyl group (which may be any of a linear, branched or cyclic group, preferably having from 1 to 6 carbon atoms, more preferably from 1 to 3 carbon atoms, and concretely includes a methyl group, an ethyl group, a propyl group, a pentyl group, a hexyl group, an isopropyl group), an alkoxy group (which may be any of a linear, branched or cyclic group, preferably having from 1 to 6 carbon atoms, more preferably from 1 to 3 carbon atoms, and concretely includes a methoxy group), an amino group or a substituted amino group (preferably an amino group substituted with an aromatic group, concretely including a diphenylamino group, an anilyl group, a tolylamino group), an aryl group (which may be a single ring or a fused ring and may be further substituted with an aryl group, concretely including a phenyl group, a biphenyl group, a terphenyl group), an electron-donating group that contains a heterocyclic structure (preferably an electron-donating group that contains a heterocyclic structure containing a nitrogen atom or a sulfur atom, concretely including a thiophenyl group, a benzothiophenyl group, a julolidyl group, a pyrrolyl group, an indolyl group, a carbazolyl group), etc. Preferably, for example, the electron-donating group has a σp value of at most −0.06, more preferably at most −0.14, even more preferably at most −0.28.

Preferably, at least one of $R^1$, $R^2$, $R^3$, $R^4$, $R^5$, $R^6$, $R^7$ and $R^8$ is an electron-donating group that contains a structure represented by any of the following general formulae (2) to (4)

[Chem. 6]

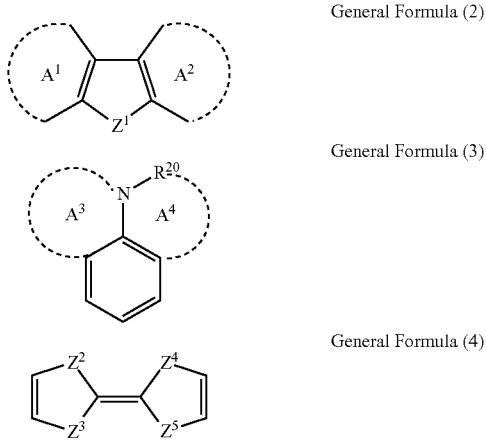

General Formula (2)

General Formula (3)

General Formula (4)

In the general formula (2), $Z^1$ represents a nitrogen atom, an oxygen atom, a sulfur atom or a silicon atom. In the general formula (2), $A^1$ and $A^2$ may form, each independently, an aromatic ring, a heteroaromatic ring, an aliphatic ring or a nonaromatic hetero ring, or may not form such a ring. For example, when $Z^1$ is a nitrogen atom and when both $A^1$ and $A^2$ form benzene rings, the general formula (2) represents a carbazole structure. When $A^1$ forms a benzene ring but $A^2$ does not form a ring structure, the general formula (2) represents an indole structure. Further, when both $A^1$ and $A^2$ do not form a ring structure, the general formula (2) represents a pyrrole structure. Other cases are described. When $Z^1$ is a silicon atom and when both $A^1$ and $A^2$ form benzene rings, the general formula (2) represents a silafluorene structure. When $Z^1$ is a sulfur atom and when $A^1$ forms a benzene ring but $A^2$ does not form a ring structure, the general formula (2) represents a benzothiophene structure.

When $A^1$ and $A^2$ in the general formula (2) form ring structures, the ring structures may be fused ring structures of multiple rings that are fused together. Not specifically defined, such a fused ring may be one formed by fusing aromatic rings together, or may be one formed by fusing heteroaromatic rings together, or may be one formed by fusing aliphatic rings together, or may further be any other that is formed by fusing different types of rings, such as an aromatic ring and a heteroaromatic ring. The rings to be fused together may be the same or different. For example, when $Z^1$ is a sulfur atom, when $A^1$ forms a ring structure of a furan ring fused to a benzene ring, and when $A^2$ does not form a ring structure, the general formula (2) represents a benzodifuran structure.

The ring structure that $A^1$ and $A^2$ in the general formula (2) may form is preferably an aromatic ring or a heteroaromatic ring, more preferably an aromatic ring.

The aromatic ring that $A^1$ and $A^2$ may form is a benzene ring. The heteroaromatic ring that $A^1$ and $A^2$ may form includes, for example, a furan ring, a thiophene ring, a pyrrole ring, an oxazole ring, an isoxazole ring, a thiazole ring, an isothiazole ring, an imidazole ring, a pyrazole ring, a furazane ring, a pyridine ring, a pyridazine ring, a pyrimidine ring, a pyrazine ring. The aliphatic ring that $A^1$ and $A^2$ may form includes a cyclopentene ring, a cyclohexene ring, a cycloheptene ring, a cyclopentadiene ring, a cyclohexadiene ring, a cycloheptadiene ring, a cycloheptatriene ring. The nonaromatic hetero ring that $A^1$ and $A^2$ may form includes, for example, a pyrroline ring, an imidazoline ring, a pyrazoline ring. The fused ring that $A^1$ and $A^2$ may form includes, for example, a naphthalene ring, an anthracene ring, a phenanthrene ring, a pyrene ring, an indole ring, an isoindole ring, an indazole ring, a chromene ring, a quinoline ring, an isoquinoline ring, a cinnoline ring, a quinazoline ring, a quinoxaline ring, a phthalazine ring, a puteridine ring, a xanthene ring, a carbazole ring, a phenanthridine ring, an acridine ring, a phenazine ring, a phenanthroline ring, etc.

In the general formula (3), $R^{20}$ represents a hydrogen atom, an aryl group or an atomic group necessary for forming the ring structure represented by $A^4$. In the general formula (3), $A^3$ and $A^4$ may form, each independently, a heteroaromatic ring or a nonaromatic hetero ring, or may not form such a ring. For specific examples of the heteroaromatic ring and the nonaromatic hetero ring that $A^3$ and $A^4$ may form, referred to are the specific examples of the heteroaromatic ring or the nonaromatic hetero ring that the above-mentioned $A^1$ and $A^2$ may form. The aryl group that $R^{20}$ may take may have a fused structure of two or more aromatic rings fused together. The ring-constituting carbon number of the aryl group is preferably from 6 to 22, more preferably from 6 to 18, even more preferably from 6 to 14, still more preferably from 6 to 10 (i.e., benzene ring, naphthalene ring). Most preferred is a phenyl group.

Examples of the structure represented by the general formula (3) are described. For example, when $R^{20}$ is a hydrogen atom and when $A^3$ does not form a ring structure, the general formula (3) represents an aniline structure. When $R^{20}$ is a benzene ring and when $A^3$ does not form a ring structure, the general formula (3) represents a diphenylamine structure. Further, when $R^{20}$ is an atomic group necessary for forming a piperidine ring and when $A^3$ forms a piperidine ring, the general formula (3) represents a julolidine structure.

In the general formula (4), $Z^1$, $Z^2$, $Z^3$ and $Z^4$ each independently represent an oxygen atom or a sulfur atom. These atoms may be the same or different, but preferably these are the same.

Preferred examples of the ring structure represented by the general formulae (2) to (4) are listed below. However, the ring structures that may be employed in the invention should not be limitatively interpreted by these specific examples.

[Chem. 7]

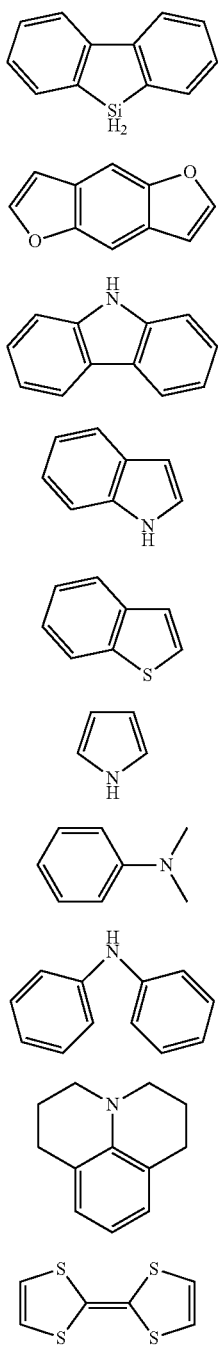

The atom or the atomic group bonding to the structure represented by the general formulae (2) to (4) may be so selected that the substituent could exhibit an electron-donating property as a whole. Typical substituents that may bond to these structures include an alkyl group, an alkoxy group, an aryl group, an aryloxy group. Also preferably, an electron-donating group is employed as the substituent.

The alkyl group as referred to in this description may be linear, branched or cyclic. Preferred is a linear or branched alkyl group. The carbon number of the alkyl group is preferably from 1 to 20, more preferably from 1 to 12, even more preferably from 1 to 6, still more preferably from 1 to 3 (i.e., a methyl group, an ethyl group, an n-propyl group, an isopropyl group). The cyclic alkyl group includes, for example, a cyclopentyl group, a cyclohexyl group, a cycloheptyl group.

The aryl group as referred to in this description may be one comprising one aromatic ring, or may have a fused structure of two or more aromatic rings fused together. The ring-constituting carbon number of the aryl group is preferably from 6 to 22, more preferably from 6 to 18, furthermore preferably from 6 to 14, even more preferably from 6 to 10 (i.e., a phenyl group, a 1-naphthyl group, a 2-naphthyl group). Most preferred is a phenyl group.

The aryloxy group as referred to in this description may be linear, branched or cyclic. Preferred is a linear or branched alkoxy group. The carbon number of the alkoxy group is preferably from 1 to 20, more preferably from 1 to 12, even more preferably from 1 to 6, still more preferably from 1 to 3 (i.e., a methoxy group, an ethoxy group, an n-propoxy group, an isopropoxy group). The cyclic alkoxy group includes, for example, a cyclopentyloxy group, a cyclohexyloxy group, a cycloheptyloxy group.

The aryloxy group as referred to in this description may be one comprising one aromatic ring, or may have a fused structure of two or more aromatic ring fused together. The carbon number of the aryloxy group is preferably from 6 to 22, more preferably from 6 to 18, even more preferably from 6 to 14, still more preferably from 6 to 10 (i.e., a phenyloxy group, a 1-naphthyloxy group, a 2-naphthyloxy group).

In the general formula (1), $R^9$, $R^{10}$, $R^{11}$, $R^{12}$, $R^{13}$, $R^{14}$, $R^{15}$ and $R^{16}$ each independently represent a hydrogen atom or an electron-withdrawing group. However, at least one of these is an electron-withdrawing group. When two or more of these are electron-withdrawing groups, those two or more electron-withdrawing groups may be the same or different. Preferably, the groups are the same. Of $R^9$, $R^{10}$, $R^{11}$, $R^{12}$, $R^{13}$, $R^{14}$, $R^{15}$ and $R^{16}$, preferably, any one or more of $R^{10}$, $R^{11}$, $R^{12}$, $R^{13}$, $R^{14}$ and $R^{15}$, more preferably two or more are electron-withdrawing groups. More preferably, any one or more of $R^{10}$, $R^{11}$, $R^{14}$ and $R^{15}$, even more preferably two or more of these are electron-withdrawing groups. Still more preferably, any one or more of, $R^{10}$, $R^{11}$, $R^{14}$ and $R^{15}$, further more preferably two or more of these are electron-withdrawing groups. In case where two or more are electron-withdrawing groups, preferably, any one of $R^{10}$ and $R^{11}$ and any one of $R^{14}$ and $R^{15}$ are electron-withdrawing groups.

The electron-withdrawing group to be represented by $R^9$, $R^{10}$, $R^{11}$, $R^{12}$, $R^{13}$, $R^{14}$, $R^{15}$ and $R^{16}$ in the general formula (1) is a group which, when bonding to the spirobifluorene ring, exhibits a property of withdrawing an electron from the spirobifluorene ring. The electron-withdrawing group may be any of an aromatic group, a heteroaromatic group or an aliphatic group, or may be a composite group formed of two or more of these groups. Examples of the electron-withdrawing group include a nitro group, a perfluoroalkyl group (preferably having from 1 to 6 carbon atoms, more preferably from 1 to 3 carbon atoms, and concretely including a trifluoromethyl group), a sulfonyl group, an electron-withdrawing group that has a heterocyclic structure (the electron-withdrawing group of the type includes, for example, those except a triazino group, preferably an electron-withdrawing group that contains a heterocyclic structure containing a nitrogen atom or a sulfur atom, and specific examples thereof include an oxadiazolyl group, a benzothiadiazolyl group, a tetrazolyl group, a thiazolyl group, an imidazolyl group, etc.), a phosphine oxide structure-containing group, a cyano group, etc. Preferably, the electron-withdrawing group has, for example, a σp value of at least 0.02, more preferably at least 0.34, even more preferably at least 0.62. Preferred examples of the electron-withdrawing group include a cyano group and a group having a higher electron-withdrawing capability than a cyano group (for example, a nitro group).

As the family of the compounds represented by the general formula (1), there may be defined various types of compound groups. For example, there may be mentioned a compound family where at least one of $R^1$, $R^2$, $R^3$, $R^4$, $R^5$, $R^6$, $R^7$ and $R^8$ is a diarylamino group optionally substituted with an electron-donating group, and at least one of $R^9$, $R^{10}$, $R^{11}$, $R^{12}$ $R^{13}$, $R^{14}$, $R^{15}$ and $R^{16}$ is a cyano group; and any other compound family of the general formula (1) from which the previous compound family is excluded.

Another family of the compounds represented by the general formula (1) includes, for example, those where from 11 to 14 of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are hydrogen atoms. In this, preferably, from 4 to 7 of $R^1$, $R^2$, $R^3$, $R^4$, $R^5$, $R^6$, $R^7$ and $R^8$ are hydrogen atoms, more preferably 6 or 7 of these are hydrogen atoms. Also preferably, from 4 to 7 of $R^9$, $R^{10}$, $R^{11}$, $R^{12}$, $R^{13}$, $R^{14}$, $R^{15}$ and $R^{16}$ are hydrogen atoms, more preferably 6 of 7 of these are hydrogen atoms. Preferred examples include those where 7 of $R^1$, $R^2$, $R^3$, $R^4$, $R^5$, $R^6$, $R^7$ and $R^8$ are hydrogen atoms, and 7 of $R^9$, $R^{10}$, $R^{11}$, $R^{12}$, $R^{13}$, $R^{14}$, $R^{15}$ and $R^{16}$ are hydrogen atoms, and those where 6 of $R^1$, $R^2$, $R^3$, $R^4$, $R^5$, $R^6$, $R^7$ and $R^8$ are hydrogen atoms, and 6 of $R^9$, $R^{10}$, $R^{11}$, $R^{12}$, $R^{13}$, $R^{14}$, $R^{15}$ and $R^{16}$ are hydrogen atoms.

Still another family of the compounds represented by the general formula (1) includes, for example, a family of monospirobifluorene compounds. In the compound family of the type, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are not a group that contains a spirobifluorene ring.

Still another family of the compounds represented by the general formula (1) includes those represented by the following general formula (1'). The general formula (1') includes novel compounds.

[Chem. 8]

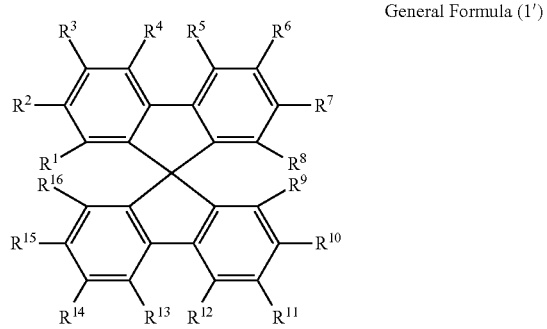

General Formula (1')

[In the general formula (1'), $R^1$, $R^2$, $R^3$, $R^4$, $R^5$, $R^6$, $R^7$ and $R^8$ each independently represent a hydrogen atom or an electron-donating group, and at least one of these is an electron-donating group that contains a structure represented by any of the above-mentioned general formulae (2) to (4). $R^9$, $R^{10}$, $R^{11}$, $R^{12}$, $R^{13}$, $R^{14}$, $R^{15}$ and $R^{16}$ each independently represent a hydrogen atom or an electron-withdrawing group, and at least one of these is an electron-withdrawing group.]

In the general formula (1'), preferably, at least one of $R^1$, $R^2$, $R^3$, $R^4$, $R^5$, $R^6$, $R^7$ and $R^8$ is an electron-donating group that contains a structure represented by any of the above-mentioned D1 to D8. Also preferably, at least one of $R^1$, $R^2R^3$, $R^4$, $R^5$, $R^6$, $R^7$ and $R^8$ is an electron-donating group that contains a structure represented by the above-mentioned D9. Of those, further mentioned are a family of compounds where the electron-withdrawing group is a cyano group, a family of compounds having two or more electron-donating groups and two or more electron-withdrawing groups, as well as a compound 10 to be produced in Synthesis Example 1 as given hereinunder and its derivatives.

The molecular weight of the compound represented by the general formula (1) is, for example, when an organic layer containing the compound is intended to be formed through vapor deposition in use thereof, preferably at most 1500, more preferably at most 1200, even more preferably at most 1000, still more preferably at most 800. The lower limit of the molecular weight may be, for example, at least 350.

Specific examples of the compound represented by the general formula (1) are shown below. However, the compound represented by the general formula (1) for use in the invention should not be limitatively interpreted by these specific examples. In the Tables, D1 to D10 each represent an unsubstituted electron-donating group that has the above-mentioned structure, CN represents a cyano group and H represents a hydrogen atom.

[Chem. 9]

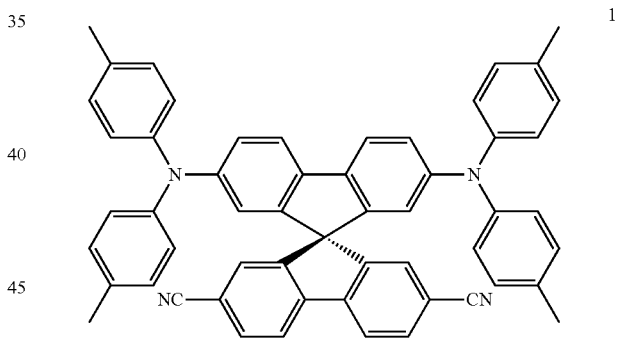

TABLE 1

| Compound No. | $R^2$ | $R^7$ | $R^{10}$ | $R^{15}$ | Other R |
|---|---|---|---|---|---|
| 2 | D1 | D1 | CN | CN | H |
| 3 | D2 | D2 | CN | CN | H |
| 4 | D3 | D3 | CN | CN | H |
| 5 | D4 | D4 | CN | CN | H |
| 6 | D5 | D5 | CN | CN | H |
| 7 | D6 | D6 | CN | CN | H |
| 8 | D7 | D7 | CN | CN | H |
| 9 | D8 | D8 | CN | CN | H |
| 10 | D9 | D9 | CN | CN | H |
| 11 | D10 | D10 | CN | CN | H |
| 12 | H | D1 | H | CN | H |
| 13 | H | D2 | H | CN | H |
| 14 | H | D3 | H | CN | H |
| 15 | H | D4 | H | CN | H |
| 16 | H | D5 | H | CN | H |
| 17 | H | D6 | H | CN | H |
| 18 | H | D7 | H | CN | H |

TABLE 1-continued

| Compound No. | $R^2$ | $R^7$ | $R^{10}$ | $R^{15}$ | Other R |
|---|---|---|---|---|---|
| 19 | H | D8 | H | CN | H |
| 20 | H | D9 | H | CN | H |
| 21 | H | D10 | H | CN | H |

TABLE 2

| Compound No. | $R^3$ | $R^6$ | $R^{11}$ | $R^{14}$ | Other R |
|---|---|---|---|---|---|
| 22 | D1 | D1 | CN | CN | H |
| 23 | D2 | D2 | CN | CN | H |
| 24 | D3 | D3 | CN | CN | H |
| 25 | D4 | D4 | CN | CN | H |
| 26 | D5 | D5 | CN | CN | H |
| 27 | D6 | D6 | CN | CN | H |
| 28 | D7 | D7 | CN | CN | H |
| 29 | D8 | D8 | CN | CN | H |
| 30 | D9 | D9 | CN | CN | H |
| 31 | D10 | D10 | CN | CN | H |
| 32 | H | D1 | H | CN | H |
| 33 | H | D2 | H | CN | H |
| 34 | H | D3 | H | CN | H |
| 35 | H | D4 | H | CN | H |
| 36 | H | D5 | H | CN | H |
| 37 | H | D6 | H | CN | H |
| 38 | H | D7 | H | CN | H |
| 39 | H | D8 | H | CN | H |
| 40 | H | D9 | H | CN | H |
| 41 | H | D10 | H | CN | H |

The above compound 4 having two 9-carbazolyl groups is a known compound, and can be produced by combining known compound production methods. For example, the compound 1 can be produced by di-iodizing 2,7-dicyanospirobifluorene with an iodizing agent to give 2',7'-di-iodized-2,7-dicyanospirobifluorene followed by further reaction with diphenylamine. In addition, the compound of the invention may also be produced by di-bromidizing a substituted spirobifluorene followed by reaction with a boronic acid having, for example, a structure of D1 to D10. The other compounds of the invention may be produced by optionally modifying these methods or by combining the method with any known production method. For the reaction condition in each step, known reaction conditions may be suitably selected and employed.

[Organic Electroluminescence Element]

The organic electroluminescence element of the invention is provided with a configuration having an anode, a cathode and an organic layer between the anode and the cathode. The organic layer contains at least a light-emitting layer, and may be a light-emitting layer alone or may have any one or more organic layers in addition to a light-emitting layer. The organic electroluminescence element of the invention contains the compound represented by the general formula (1) in the light-emitting layer therein.

When the compound represented by the general formula (1) is used in the light-emitting layer of an organic electroluminescence element as a thermally-activated delayed fluorescence material, then the element secures a high emission efficiency more inexpensively than before. Heretofore, for producing an organic electroluminescence element having a high emission efficiency, there have been actively made studies using a phosphorescence material having a high exciton production efficiency. However, using a phosphorescence material has a problem in that the cost is high as requiring use of a rare metal such as Ir or Pt. Using a delayed fluorescence material does not require such an expensive material, therefore making it possible to inexpensively provide an organic electroluminescence element having a high emission efficiency. In particular, the compound represented by the general formula (1) has an extremely small energy difference between T1 level and S1 level ($\Delta E_{ST}$) as compared with conventional delayed fluorescence materials. Further, the organic electroluminescence element using the compound represented by the general formula (1) can markedly increase the external quantum efficiency which has heretofore been low. Of the organic electroluminescence element of the invention, the current efficiency, the power efficiency and the luminance are all extremely high, and at present reach the level the organic electroluminescence element of the invention the organic electroluminescence element of the invention of the world's best technology; and therefore, the organic electroluminescence element of the invention is extremely useful.

The organic electroluminescence element of the invention has a laminate configuration of at least an anode, an organic layer and a cathode. A single-layer organic electroluminescence element may comprise a light-emitting layer alone between the anode and the cathode; however, it is desirable that the organic electroluminescence element of the invention is provided with multiple organic layers. The other organic layers than the light-emitting layer may be referred to as a hole injection layer, a hole transport layer, an electron block layer, a light-emitting layer, a hole blocking layer, an electron transport layer, an electron injection layer or the like, depending on the functions thereof, for which any known material may be used as suitably combined. As specific configuration examples including an anode and a cathode, there may be mentioned anode/light-emitting layer/cathode, anode/hole injection layer/light-emitting layer/cathode, anode/hole injection layer/hole transport layer/light-emitting layer/cathode, anode/hole injection layer/light-emitting layer/electron injection layer/cathode, anode/hole injection layer/hole transport layer/light-emitting layer/electron injection layer/cathode, anode/hole injection layer/light-emitting layer/electron transport layer/electron injection layer/cathode, anode/hole injection layer/hole transport layer/light-emitting layer/electron transport layer/electron injection layer/cathode, anode/light-emitting layer/electron injection layer/cathode, anode/light-emitting layer/electron injection layer/electron transport layer/cathode, anode/hole injection layer/light-emitting layer/hole blocking layer/electron injection layer/cathode. The configuration of anode/organic layer/cathode may be formed on a substrate. The configurations that may be employed in the invention should not be limited to those exemplifications. Especially preferably, the compound represented by the general formula (1) is used in the light-emitting layer, which, however, does not exclude use of the compound represented by the general formula (1) in the other organic layer than the light-emitting layer as a charge transport material or the like therein.

In producing the organic layers and the electrodes that constitute the organic electroluminescence element of the invention, any known production methods may be employed as suitably selected. In addition, various materials generally employed in known organic electroluminescence elements can be selected and used in those organic layers and electrodes. Further, various modifications of known techniques and those that may be readily anticipated from known techniques may be optionally applied to the organic electroluminescence element of the invention. Typical materials of constituting the organic electroluminescence element of the invention are described below; however, the materials usable for the organic electroluminescence element of the invention should not be limitatively interpreted by the following description.

(Substrate)

The substrate functions as a support of supporting the configuration of anode/organic layer/cathode and further functions as a substrate in producing the configuration of anode/organic layer/cathode. The substrate may be formed of a transparent material, or may also be formed of a semitransparent or nontransparent material. In case where emitted light is taken out from the side of the anode, a transparent substrate is preferably used. The material to constitute the substrate includes glass, quartz, metal, polycarbonate, polyester, polymethacrylate, polysulfone. When a flexible substrate is used, then there may be provided a flexible organic electroluminescence element.

(Anode)

The anode has a function of injecting holes toward the organic layer. As the anode, preferably used is a material having a high work function. For example, a material having a work function of at least 4 eV is preferably used. Concretely, there are mentioned metals (for example, aluminium, gold, silver, nickel, palladium, platinum), metal oxides (for example, indium oxide, tin oxide, zinc oxide, mixture of indium oxide and tin oxide [ITO], mixture of zinc oxide and indium oxide [IZO]), metal halides (for example, copper iodide), carbon black. In addition, also employable are electroconductive polymers such as polyaniline, poly(3-methylthiophene), polypyrrole, etc. In case where emitted light is taken out from the side of the anode, preferred is use of a material having a high light transmittance for the emitted light, such as ITO, IZO or the like. The transmittance is preferably at least 10%, more preferably at least 50%, even more preferably at least 80%. The thickness of the anode is generally at least 3 nm, but preferably at least 10 nm. The upper limit may be, for example, at most 1 μm, however, when the anode is not required to have transparency, the thickness thereof may be further thicker, and for example, such a thick anode may additionally serve also as the above-mentioned substrate. The anode may be formed, for example, according to a vapor deposition method, a sputtering method, or a coating method. In case where an electroconductive polymer is used for the anode, the anode may be formed on the substrate according to an electrolytic polymerization method. After the anode formation, the surface may be processed for the purpose of improving the hole injection function thereof. Specific examples of the surface treatment include plasma treatment (for example, argon plasma treatment, oxygen plasma treatment), UV treatment, ozone treatment, etc.

(Hole Injection Layer and Hole Transport Layer)

The hole injection layer has a function of transporting holes from the anode to the side of the light-emitting layer. The hole injection layer is formed generally on the anode, and therefore the layer is preferably excellent in the adhesiveness to the anode surface. Consequently, it is desirable that the layer is formed of a material having good thin-film formability. The hole transport layer has a function of transporting holes to the side of the light-emitting layer. The hole transport layer is formed of a material having excellent hole transportability.

For the hole injection layer and the hole transport layer, used are hole transport materials having a high hole mobility and a small ionization energy. The ionization energy of the material is, for example, preferably from 4.5 to 6.0 eV. As the hole transport material, various materials that are said to be usable as the hole injection layer or the hole transport layer of organic electroluminescence elements may be used here as suitably selected. The hole transport material may be a polymer material having a recurring unit or may also be a low-molecular compound.

As the hole transport material, for example, there may be mentioned aromatic tertiary amine compounds, styrylamine compounds, oxadiazole derivatives, imidazole derivatives, triazole derivatives, pyrazoline derivatives, pyrazolone derivatives, phenylenediamine derivatives, arylamine derivatives, amino-substituted chalcone derivatives, oxazole derivatives, polyarylalkane derivatives, styrylanthracene derivatives, fluorenone derivatives, hydrazone derivatives, stilbene derivatives, silazane derivatives, silane polymers, aniline copolymers, thiophene polymers, porphyrin compounds.

As a preferred hole transport material, there are mentioned aromatic tertiary amine compounds, concretely including triphenylamine, tritolylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane, N,N'-bis(4'-diphenylamino-4-biphenylyl)-N,N'-diphenylbenzidine, N,N'-bis(4'-diphenylamino-4-phenyl)-N,N'-diphenylbenzidine, N,N'-bis(4'-diphenylamino-4-phenyl)-N,N'-di(1-naphthyl)benzidine, N,N'-bis(4'-phenyl(1-naphthyl)amino-4-phenyl)-N,N'-diphenyl benzidine, N,N'-bis(4'-phenyl(1-naphthyl)amino-4-phenyl)-N,N'-di(1-naphthyl)benzidine, etc. Also as a preferred hole transport material, phthalocyanine compounds are mentioned. Concretely, there are mentioned $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, GaPc-O-GaPc [Pc means phthalocyanine]. Further, also preferred is use of poly(ethylenedioxy)thiophene (PEDOT), metal oxides such as molybdenum oxide and the like, and known aniline derivatives.

One alone or two or more different types of hole transport materials may be used in one layer, either singly or as combined therein. The hole injection layer and the hole transport layer may be formed, for example, according to a vapor deposition method, a sputtering method or a coating method. The thickness of the hole injection layer and the hole transport layer may be generally at least 3 nm each but preferably at least 10 nm each. The upper limit may be, for example, at most 5 μm each.

(Light-Emitting Layer)

The light-emitting layer in the organic electroluminescence element of the invention may contain a host material and a dopant material, or may be formed of a single material. The light-emitting layer in the organic electroluminescence element of the invention contains the compound represented by the general formula (1).

When the light-emitting layer contains a host material and a dopant material, preferably, the amount of the dopant material is at most 10% by weight of the host material therein for the purpose of preventing concentration quenching, more preferably at most 6% by weight. One material alone or two or more different types of materials may be used either singly or as combined for the dopant material and the host material. The doping may be attained by co-deposition of the host material and the dopant material, in which the host material and the dopant material may be previously mixed for simultaneous vapor deposition.

As the host material for use in the light-emitting layer, there are mentioned carbazole derivatives, quinolinol derivative metal complexes, oxadiazole derivatives, distyrylarylene derivatives, diphenylanthracene derivatives, etc. In addition to these, also usable here are those that are proposed as the host material in a light-emitting layer, as suitably selected. As a preferred host material, for example, there are mentioned the compounds represented by the following general formula (10):

[Chem. 10]

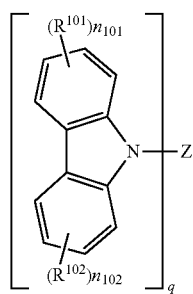

General Formula (10)

In the general formula (10), Z represents a q-valent linking group; and q indicates an integer of from 2 to 4. $R^{101}$ and $R^{102}$ each independently represent a substituent; and n101 and n102 each independently indicate an integer of from 0 to 4. When n101 is an integer of from 2 to 4, n101's $R^{101}$'s may be the same or different; and when n102 is an integer of from 2 to 4, n102's, $R^{102}$'s may be the same or different. Further, $R^{101}$, $R^{102}$, n101 and n102 in q's constitutive elements may be the same or different.

As the substituent represented by $R^{101}$ and $R^{102}$ in the general formula (10) includes, for example, a substituted or unsubstituted alkyl group, a substituted or unsubstituted alkoxy group, a substituted or unsubstituted aryl group, a substituted or unsubstituted aryloxy group, a substituted or unsubstituted alkenyl group, a substituted or unsubstituted amino group, a halogen atom, a cyano group. Preferred are a substituted or unsubstituted alkyl group, a substituted or unsubstituted aryl group, a substituted or unsubstituted alkoxy group, a substituted or unsubstituted aryloxy group; and more preferred are a substituted or unsubstituted alkyl group, a substituted or unsubstituted aryl group.

Preferably, n101 and n102 each are independently an integer of from 0 to 3, more preferably an integer of from 0 to 2. Also preferably, both n101 and n102 are 0.

Z in the general formula (10) is preferably a linking group that contains an aromatic ring or a hetero ring. The aromatic ring may be a single ring or a fused ring of two or more aromatic rings fused together. The carbon number of the aromatic ring is preferably from 6 to 22, more preferably from 6 to 18, even more preferably from 6 to 14, still more preferably from 6 to 10. Specific examples of the aromatic ring include a benzene ring and a naphthalene ring. The hetero ring may be a single ring, or a fused ring of one or more hetero ring fused with an aromatic ring or a hetero ring. The carbon number of the hetero ring is preferably from 5 to 22, more preferably from 5 to 18, even more preferably from 5 to 14, still more preferably from 5 to 10. Preferably, the hetero atom to constitute the hetero ring is a nitrogen atom. Specific examples of the hetero ring include a pyridine ring, a pyridazine ring, a pyrimidine ring, a triazine ring, a triazole ring, a benzotriazole ring. Z in the general formula (10) may contain an aromatic ring or a hetero ring and may additionally contain a nonaromatic linking group. The nonaromatic linking group includes the following structures:

[Chem. 11]

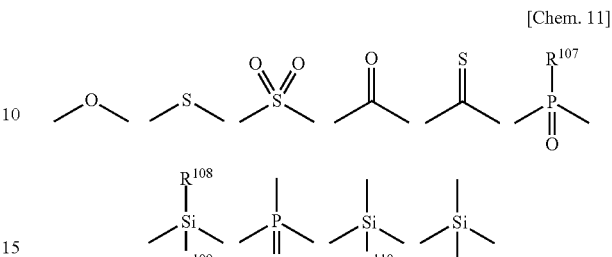

$R^{107}$, $R^{108}$, $R^{109}$ and $R^{110}$ in the above nonaromatic linking group each independently represent a hydrogen atom, a substituted or unsubstituted alkyl group or a substituted or unsubstituted aryl group, but preferably a substituted or unsubstituted alkyl group or a substituted or unsubstituted aryl group.

As preferred host materials, for example, there are mentioned compounds represented by the following general formula (11):

[Chem. 12]

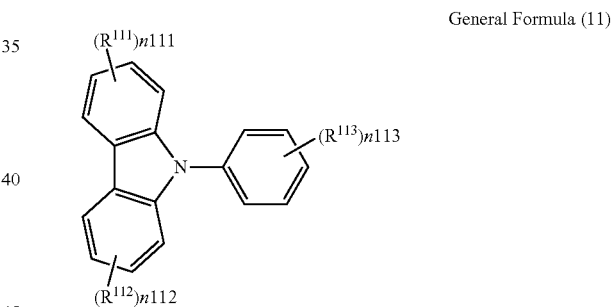

General Formula (11)

In the general formula (11), $R^{111}$, $R^{112}$ and $R^{113}$ each independently represent a substituent, n111 and n112 each independently indicate an integer of from 1 to 4, n113 indicates an integer of from 1 to 5. At least one $R^{111}$, at least one $R^{112}$, and at least one $R^{113}$ each are an aryl group. When n111 is an integer of from 2 to 4, n111's may be the same or different; when n112 is an integer of from 2 to 4, n112's $R^{112}$'s may be the same or different; and when n113 is an integer of from 2 to 5, n113's $R^{113}$'s may be the same or different.

Preferably, in the general formula (11), n111, n112 and n113 each are from 1 to 3, more preferably 1 or 2.

In the following, specific examples of the compounds represented by the general formula (10) or the general formula (11) are shown; however, the compounds represented by the general formula (10) or the general formula (11) for use in the invention should not be limitatively interpreted by these specific examples.

[Chem. 13]

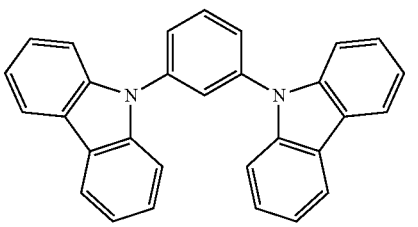

mCP

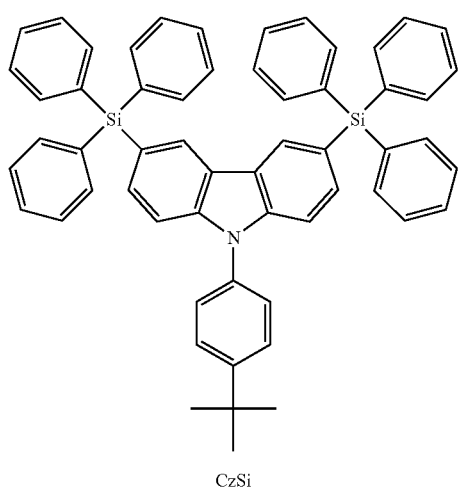

CzSi

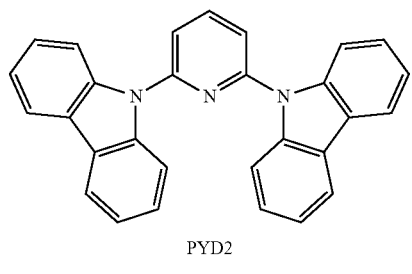

PYD2

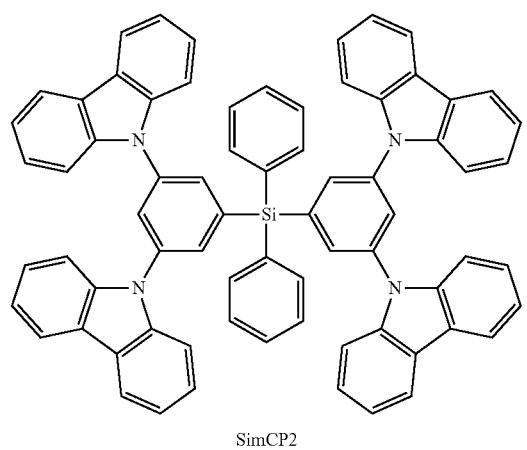

SimCP2

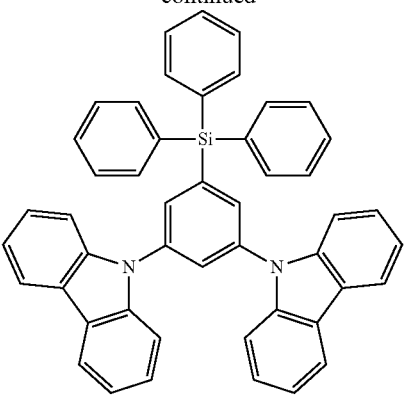

SimCP

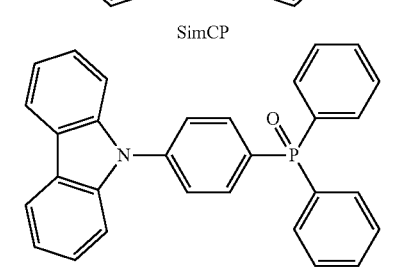

PO12

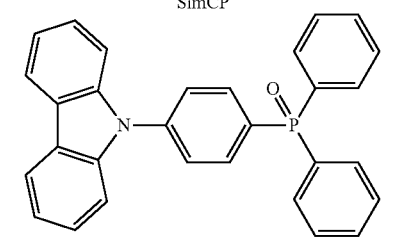

CBZ

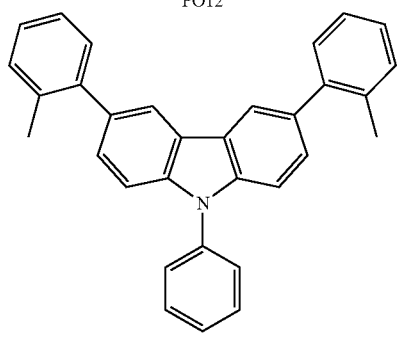

CBPE (Hole Blocking Layer)

The hole blocking layer has a function of preventing the holes having passed through the light-emitting layer from moving toward the side of cathode. Preferably, the hole blocking layer is formed between the light-emitting layer and the organic layer on the cathode side. The organic material to form the hole blocking layer includes aluminium complex compounds, gallium complex compounds, phenanthroline derivatives, silol derivatives, quinolinol derivative metal complexes, oxadiazole derivatives, oxazole derivatives. Concretely, there are mentioned bis(8-hydroxyquinolinate)(4-phenylphenolate)aluminium, bis(2-methyl-8-hydroxyquinolinate) (4-phenylphenolate)gallium, 2,9-dimethyl-4,7-diphenyl-1,10-phenanthroline (BCP), etc. One organic material alone or two or more different types of organic materials may be selected for the hole blocking layer either singly or as combined. The hole blocking layer may be formed, for example, according to a vapor deposition method, a sputtering method or a coating method. The thickness of the hole blocking layer may be generally at least 3 nm but is preferably at least 10 nm. The upper limit may be, for example, at most 5 μm.

(Electron Injection Layer and Electron Transport Layer)

The electron injection layer has a function of transporting electrons from the cathode to the side of the light-emitting layer. The electron injection layer is formed generally so as to be in contact with the cathode, and therefore the layer is preferably excellent in the adhesiveness to the cathode surface. The electron transport layer has a function of transporting electrons to the side of the light-emitting layer. The electron transport layer is formed of a material excellent in electron transportability.

For the electron injection layer and the electron transport layer, used are electron transport materials having a high electron mobility and a large ionization energy. As the electron transport material, various materials that are said to be usable as the electron injection layer or the electron transport layer of organic electroluminescence elements may be used here as suitably selected. The electron transport material may be a polymer material having a recurring unit or may also be a low-molecular compound.

As the electron transport material, for example, there may be mentioned fluorenone derivatives, anthraquinodimethane derivatives, diphenoquinone derivatives, thiopyran dioxide derivatives, oxazole derivatives, thiazole derivatives, oxadiazole derivatives, triazole derivatives, imidazole derivatives, perylenetetracarboxylic acid derivatives, quinoxaline derivatives, fluorenylidenemethane derivatives, anthraquinodimethane derivatives, anthrone derivatives, etc. Specific examples of preferred electron transport materials include 2,5-bis(1-phenyl)-1,3,4-oxazole, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbentene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, 1,4-bis[2-(5-phenyltriazolyl)]benzene, lithium 8-hydroxyquinolinate, zinc bis(8-hydroxyquinolinate), copper bis(8-hydroxyquinolinate), manganese bis(8-hydroxyquinolinate), aluminium tris(8-hydroxyquinolinate), aluminium tris(2-methyl-8-hydroxyquinolinate), gallium tris(8-hydroxyquinolinate), beryllium bis(10-hydroxybenzo[h]quinolinate), zinc bis(10-hydroxybenzo[h]quinolinate), chlorogallium bis(2-methyl-8-quinolinate), gallium bis(2-methyl-8-quinolinate)(o-cresolate), aluminium bis(2-methyl-8-quinolinate)(1-naphtholate), gallium bis(2-methyl-8-quinolinate)(2-naphtholate), etc.

One alone or two or more different types of electron transport materials may be used in one layer either singly or as suitably selected and combined. The electron injection layer and the electron transport layer may be formed, for example, according to a vapor deposition method, a sputtering method or a coating method. The thickness of the electron injection layer and the electron transport layer may be generally at least 3 nm each, preferably at least 10 nm each. The upper limit may be, for example, at most 5 μm each.

(Cathode)

The cathode has a function of injecting electrons toward the organic layer. As the cathode, preferably used is a material having a low work function. For example, a material having a work function of at most 4 eV is preferably used. Concretely, there are mentioned metals (for example, tin, magnesium, indium, calcium, aluminium, silver), and alloys (for example, aluminium-lithium alloy, magnesium-silver alloy, magnesium-indium alloy). In case where emitted light is taken out from the side of the cathode, preferred is use of a material having a high light transmittance. The transmittance is preferably at least 10%, more preferably at least 50%, even more preferably at least 80%. The thickness of the cathode is generally at least 3 nm, but preferably at least 10 nm. The upper limit may be, for example, at most 1 μm, however, when the cathode is not required to have transparency, the thickness thereof may be further thicker. The cathode may be formed, for example, according to a vapor deposition method or a sputtering method. Preferably, a protective layer is formed on the cathode for protecting the cathode. The protective layer of the type is preferably a layer formed of a metal that has a high work function and is stable. For example, a metal layer of aluminium, silver, copper, nickel, chromium, gold, platinum or the like may be formed.

The organic electroluminescence element of the invention is applicable to a variety of uses. For example, using the organic electroluminescence element of the invention, it is possible to produce organic electroluminescence display devices. For the details, referred to is "Organic EL Display" written by Shizuo Tokito, Chihaya Adachi, Yukihide Murata (Ohm Publishing). In particular, the organic electroluminescence element of the invention is applicable to organic electroluminescence lighting that is much in demand.

EXAMPLES

The characteristics of the invention are described more concretely with reference to the following Synthesis Examples, Test Examples and Production Examples. In the following Examples, the materials used, the details of the treatment and the treatment process may be suitably modified or changed not overstepping the spirit and the scope of the invention. Accordingly, the scope of the invention should not be limitatively interpreted by the Examples mentioned below.

Synthesis Example 1

Compound 10 was synthesized according to the following scheme in this Synthesis Example.

[Chem. 14]

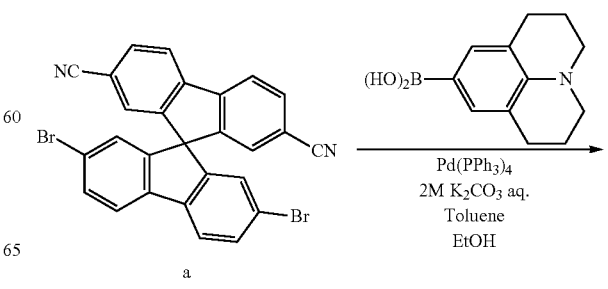

-continued

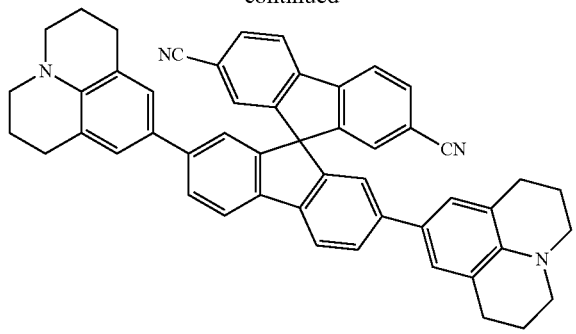

10

0.52 g (0.99 mmol, compound a) of 2,7-dibromo-2',7'-dicyano-9,9'-spirobifluorene and 0.62 g (2.9 mmol) of (2,3,6,7-tetrahydro-1H,5H-benzo[ij]quinolidin-9-yl) boronic acid were put into a 100-mL three-neck flask, and to this mixture, added were 10 ml of toluene, 2 ml of ethanol, and 3 ml of aqueous 2 M potassium carbonate solution. The mixture was bubbled with nitrogen for 20 minutes. After the bubbling, 0.090 g (0.078 mmol) of tetrakis(triphenylphosphine) palladium (0) was added to the mixture. The mixture was stirred in a nitrogen stream atmosphere at 70° C. for 21 hours. After the stirring, the mixture was added to 200 mL of toluene and 200 mL of water, and stirred. After the stirring, the organic layer and the aqueous layer were separated from each other, and the organic layer was washed with saturated saline water. After the washing, the organic layer was dried with magnesium sulfate added thereto. After the drying, the mixture was filtered under suction to give a filtrate. The obtained filtrate was concentrated, and the resulting solid was washed with methanol. After the washing, the solid was dissolved in chloroform, then hexane was added thereto for reprecipitation to give a solid. The obtained solid was purified through silica gel column chromatography (developing solvent:chloroform). After the purification, the obtained fraction was concentrated, and the solid was collected to be 0.23 g of a yellow powdery solid (compound 10). The yield was 33%.

$^1$H NMR (500 MHz, CDCl$_3$): 7.98 (d, J=8.0 Hz, 2H), 7.83 (d, J=8.0 Hz, 2H), 7.71 (d, J=8.0 Hz, 2H), 7.57 (d, J=8.0 Hz, 2H), 7.14 (s, 2H), 6.84 (s, 4H), 6.67 (s, 2H), 3.12 (d, J=11 Hz, 8H), 2.72 (t, J=6.4 Hz, 8H), 1.93 (d, J=11 Hz, 8H).

MS (MALDI): m/z Calcd: 708.33 [M+H]$^+$; Found: 708.29.

Example 1

Figure 2:
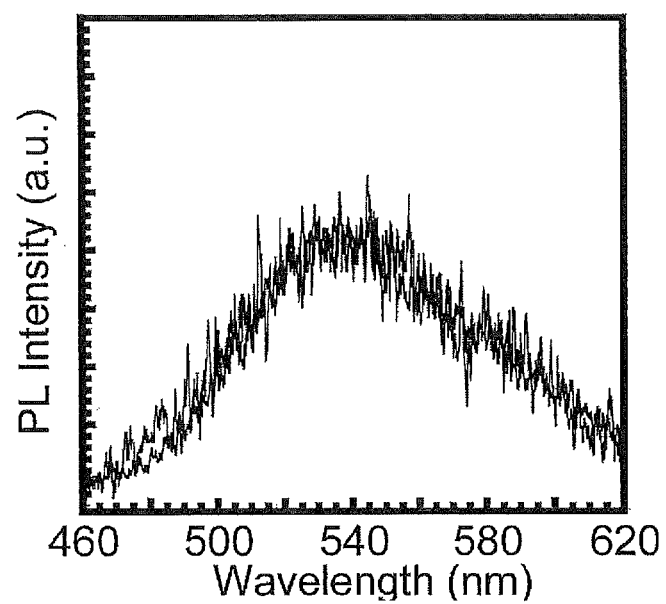
FIG. 2 This is an emission spectrum of the co-deposition film in Example 1.
Figure 3:
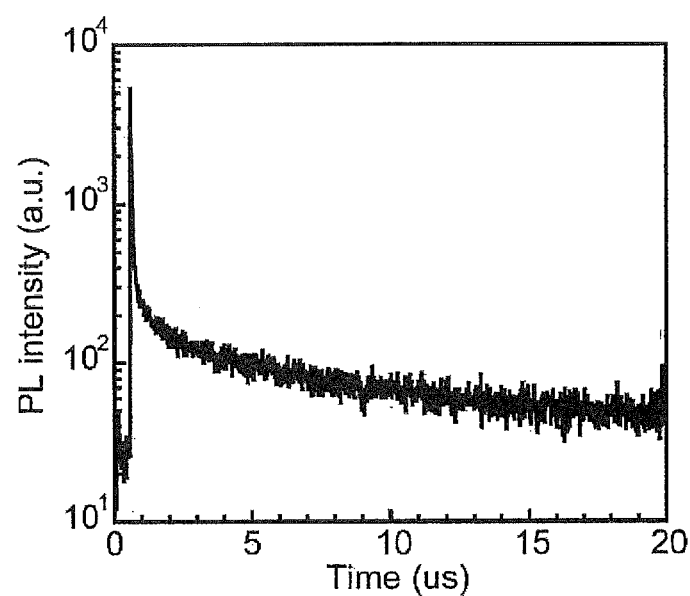
FIG. 3 This is a graph showing the PL transient decay in Example 1.

In this Example, the compound 1 was used for the test, and an organic electroluminescence element having the configuration shown in FIG. 1 was produced.
(1) Observation of Delayed Fluorescence A film was formed on a quartz substrate by co-deposition of 6 wt % compound 1 and mCP, and analyzed for the emission spectrum (FIG. 2). The co-deposition film gave yellow emission, and the PL quantum yield thereof was 27% and was high. Next, for investigating the thermally-activated delayed fluorescence characteristic of the compound 1, the co-deposition film was analyzed for the PL transient decay at 300 K, using a streak camera (FIG. 3). The PL transient decay curve well corresponded to the fitting of the two components, and showed a short-life component of 24 ns and a long-life component of 24 μs. Specifically, owing to the presence of the compound 1 therein, the film gave the thermally-activated delayed fluorescence derived from the long-life component in addition to the short-life fluorescence.

(2) Production of Organic Electroluminescence Element

On the glass 1, a film of indium/tin oxide (ITO) 2 was formed in a thickness of approximately from 30 to 100 nm, and a film of N,N'-di(naphthalen-1-yl)-N,N'-diphenylbenzidine (α-NPD) 3 was further formed thereon in a thickness of 60 nm. Next, 6 wt % compound 1 and 4,4-bis[N-(1-naphthyl)-N-phenylamino)]biphenyl (mCP) were co-deposited to form a light-emitting layer 4 in a thickness of 20 nm. Further on this, a film of 4,7-diphenyl-1,10-phenanthroline (Bphen) 5 was formed in a thickness of 40 nm. Next, a film of magnesium-silver (MgAg) 6 was vacuum-deposited in a thickness of 100 nm, and then silver (Ag) 7 was deposited thereon in a thickness of 20 nm, thereby producing an organic electroluminescence element having the configuration shown in FIG. 1.

Figure 4:
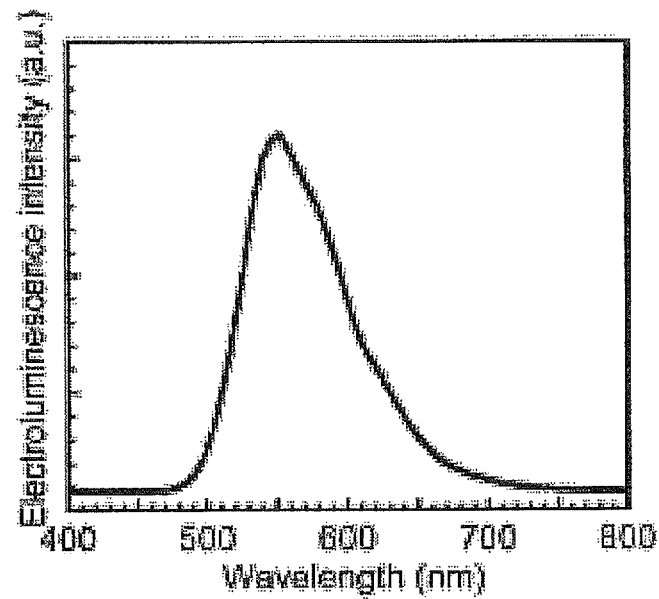
FIG. 4 This is an emission spectrum of the organic electroluminescence element in Example 1.
Figure 5:
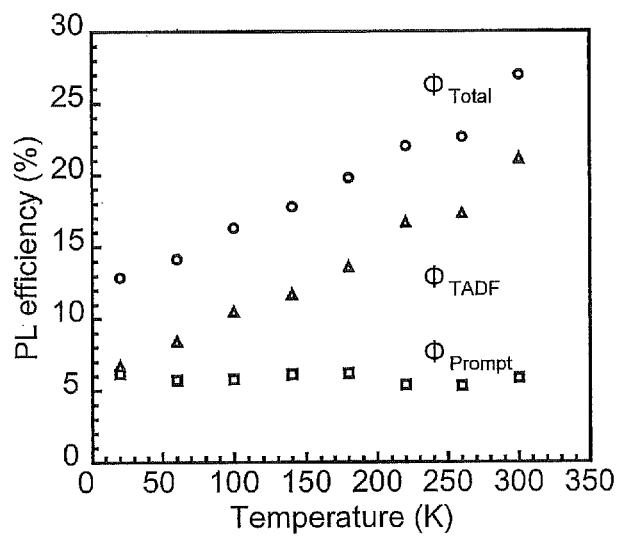
FIG. 5 This is a graph showing the relationship between the temperature and the emission efficiency in Example 1.
Figure 6:
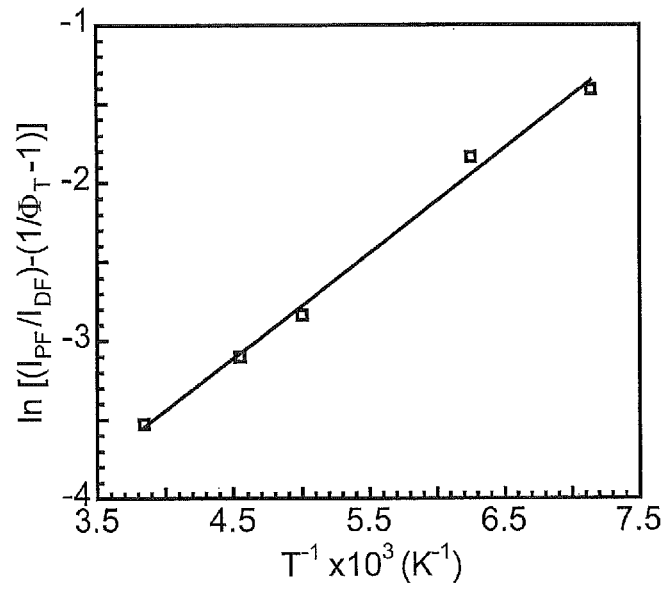
FIG. 6 This is a graph showing the relationship between the intensity ratio of the long-life emission to the prompt emission and the reciprocal of the temperature in Example 1.
Figure 7:
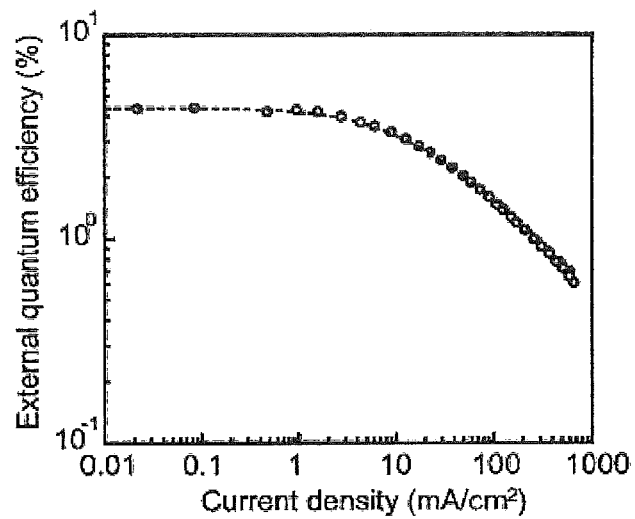
FIG. 7 This is a graph showing the relationship between the current density and the external quantum efficiency in Example 1.
Figure 8:
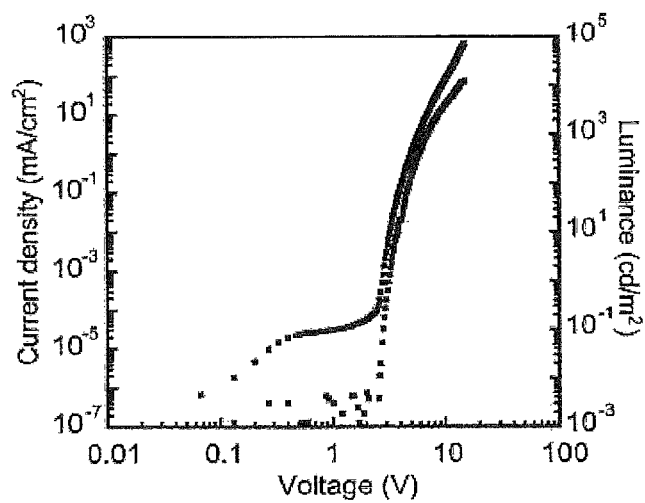
FIG. 8 This is a graph showing the current density-voltage-luminance (J-V-L) characteristic in Example 1.
Figure 9:
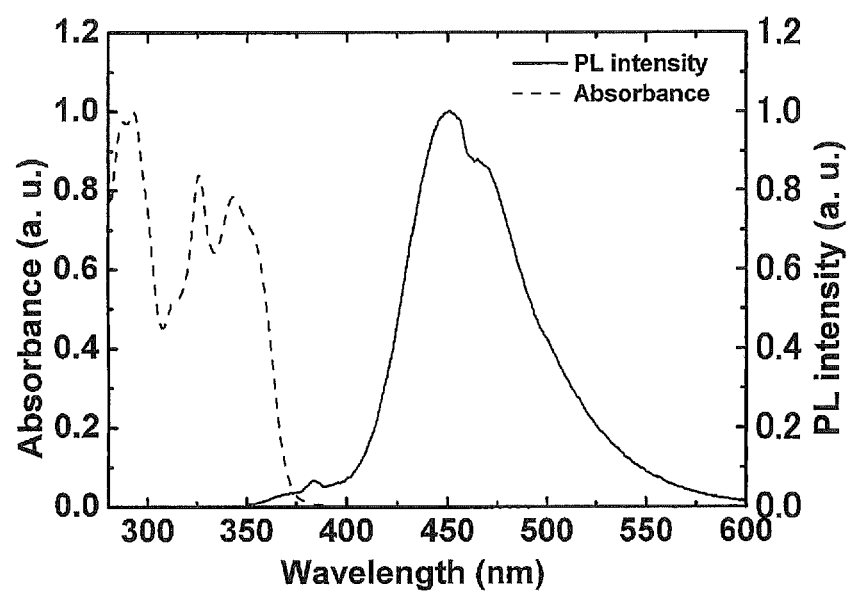
FIG. 9 This is an emission spectrum of the solution in Example 42.

Thus formed, the organic EL element was analyzed for the emission spectrum thereof, which is shown in FIG. 4. The element gave a yellow emission at the largest current. The relationship between the temperature and the emission efficiency of the element was determined, as in FIG. 5. In FIG. 5, $\Phi_{TOTAL}$ indicates total emission, $\Phi_{TADF}$ indicates long-life emission (delayed fluorescence), and $\Phi_{Prompt}$ indicates a prompt emission. Increase in $\Phi_{TADF}$ was confirmed with the temperature elevation, which confirms efficient conversion from T1 to S1. FIG. 6 is a graph showing the relationship between the reciprocal of the temperature and the intensity ratio of the long-life emission to the prompt emission (Berberan-Santos Plot). The energy difference ($\Delta E_{ST}$) between the T1 level and the S1 level was 0.057 eV, which was confirmed to be extremely small as compared with the case of conventional delayed fluorescence materials. FIG. 8 is a graph showing the relationship between the current density and the external quantum efficiency. The external quantum efficiency was 1.4% or so in conventional cases, but reached 4.4% in this Example. FIG. 9 is a graph showing the current density-voltage-luminance (J-V-L) characteristic measured by the use of a semiconductor parameter analyzer and a power meter. The element attained a current efficiency of 13.5 cd/A, a power efficiency of 13.0 Lm/W, and a luminance of 12000 cd/m$^2$ at a driving voltage 15 V.

[Chem. 15]

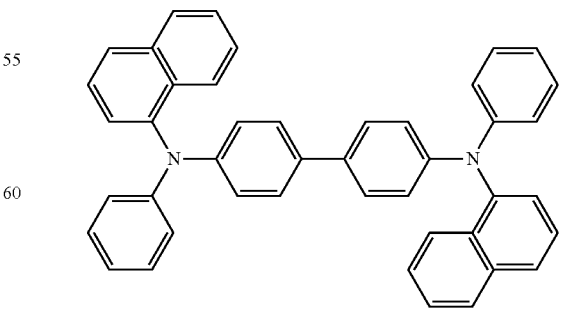

α-NPD

-continued

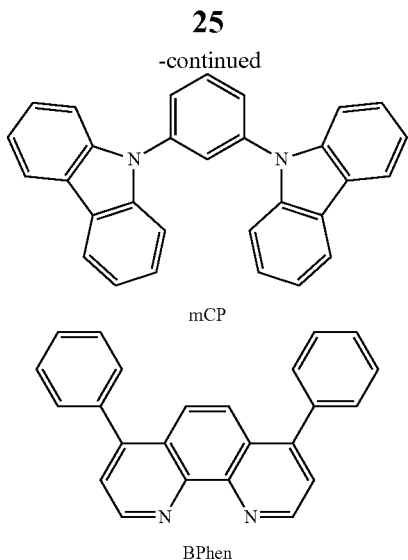

mCP

BPhen

Examples 2 to 41

In the same manner as in Example 1, the usefulness of the compounds 2 to 41 can also be confirmed.

Example 42

Figure 10:
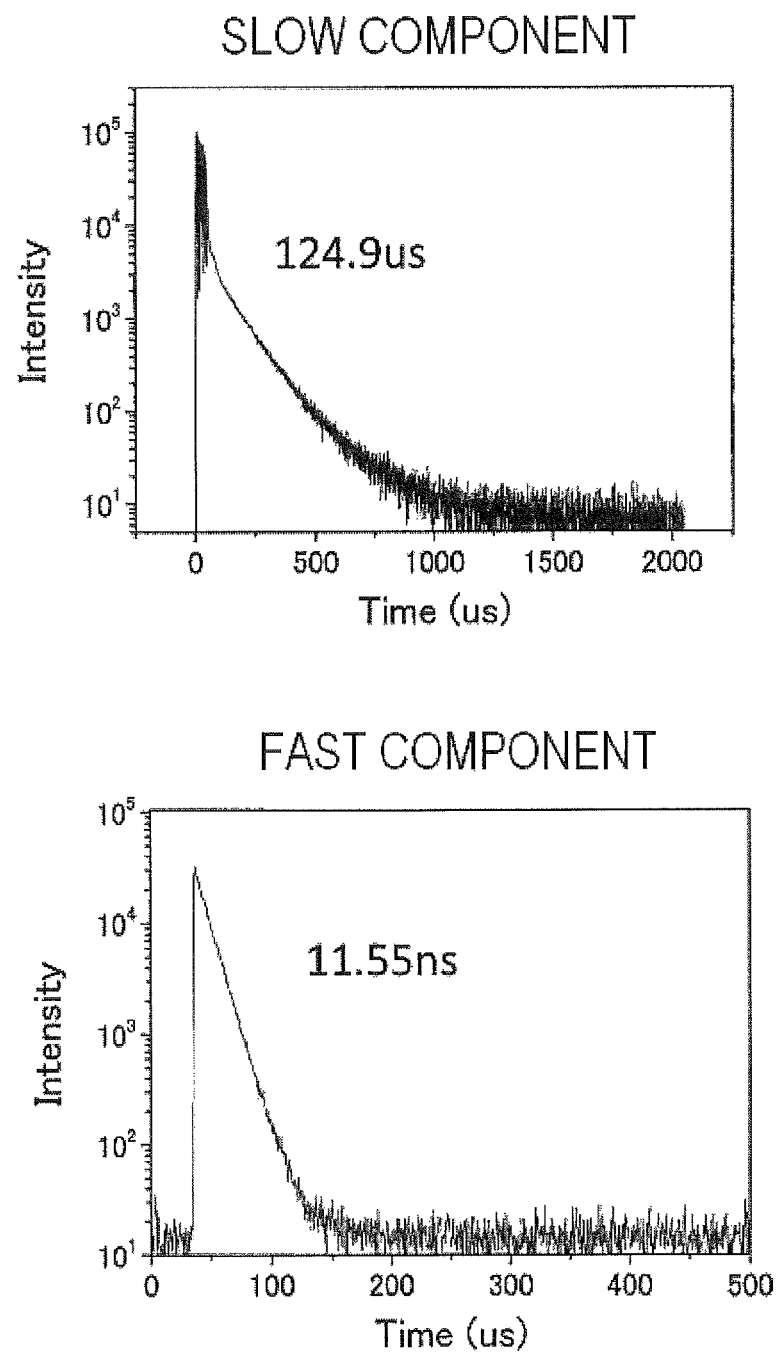
FIG. 10 This is a graph showing the PL transient decay in Example 42.

In this Example, a toluene solution of the compound 4 was prepared and the emission spectrum was measured (FIG. 9). In the same manner as in Example 1, the film was analyzed for the PL transient decay, which showed a short-life component of 11.55 ns and a long-life component of 124.9 μs (FIG. 10). Specifically, owing to the presence of the compound 4 therein, the film gave the thermally-activated delayed fluorescence derived from the long-life component in addition to the short-life fluorescence.

[Chem. 16]

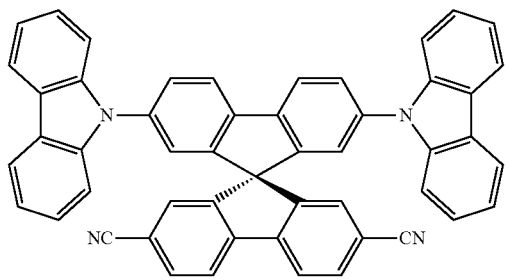

4

Example 43

Figure 11:
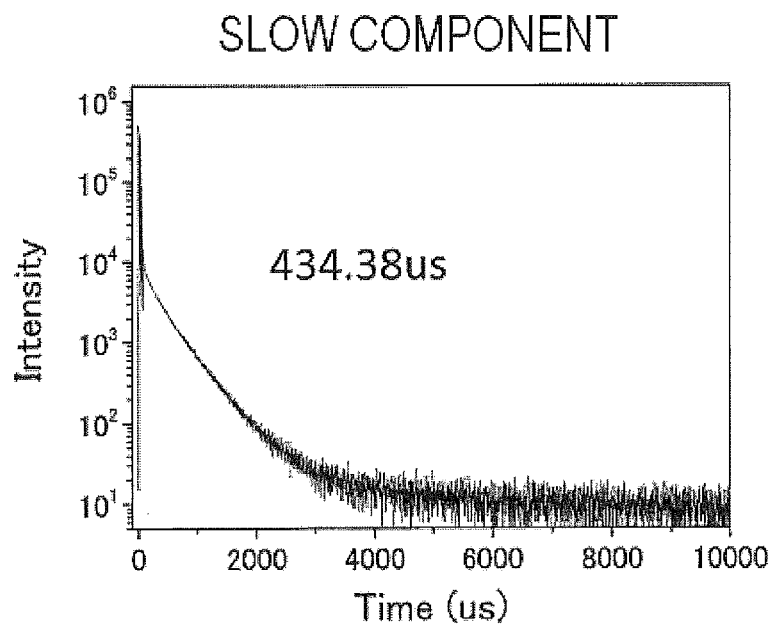
FIG. 11 This is a graph showing the PL transient decay in Example 43.
Figure 11:
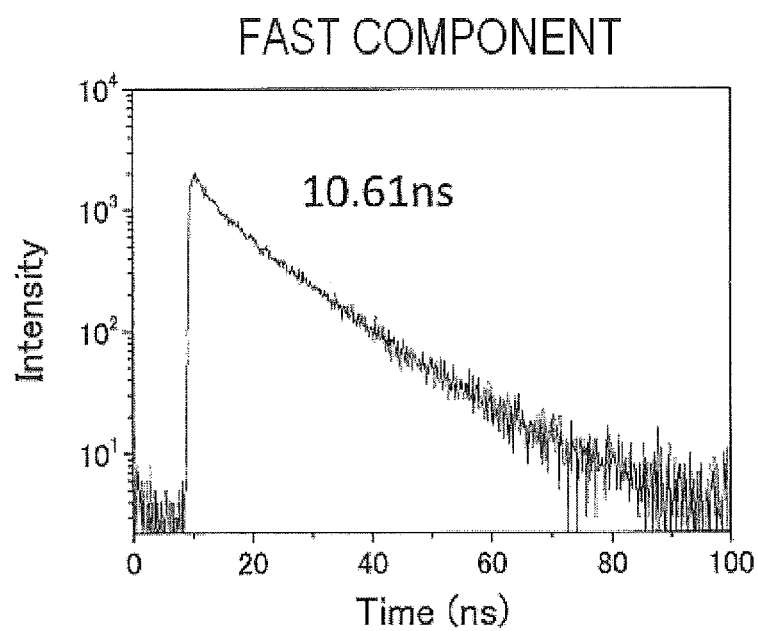

Using the compound 10 produced in Synthesis Example 1, the same solution as in Example 42 was prepared, and the emission spectrum was measured, in which light emission was seen at a peak of 550 nm. In addition, the PL transient decay was measured, which showed a short-life component of 10.61 ns and a long-life component of 434.38 μs (FIG. 11). Specifically, owing to the presence of the compound 10 therein, the film gave the thermally-activated delayed fluorescence derived from the long-life component in addition to the short-life fluorescence.

INDUSTRIAL APPLICABILITY

The organic electroluminescence element of the invention can be produced at a low cost, and can realize a high luminance with high emission efficiency. In addition, the delayed fluorescence material of the invention is useful as a light-emitting material for such organic electroluminescence elements. Consequently, the industrial applicability of the invention is great.

REFERENCE SIGNS LIST

1 Glass
2 ITO
3 mCP
4 Light-Emitting Layer
5 Bphen
6 MgAg
7 Ag

The invention claimed is:

1. A compound represented by the following general formula (1'):

General Formula (1')

[Structure showing spirobifluorene with substituents R¹ through R¹⁶]

wherein, in the general formula (1'), $R^1$, $R^2$, $R^3$, $R^4$, $R^5$, $R^6$, $R^7$ and $R^8$ each independently represent a hydrogen atom or an electron-donating group, and at least one of $R^1$, $R^2$, $R^3$, $R^4$, $R^5$, $R^6$, $R^7$ or $R^8$ is an electron-donating group that contains a structure represented by the following D9:

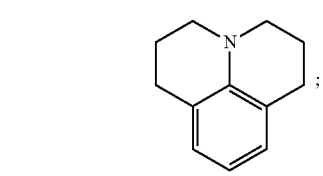

D9 and $R^9$, $R^{10}$, $R^{11}$, $R^{12}$, $R^{13}$, $R^{14}$, $R^{15}$ and $R^{16}$ each independently represent a hydrogen atom or an electron-withdrawing group, and at least one of $R^9$, $R^{10}$, $R^{11}$, $R^{12}$, $R^{13}$, $R^{14}$, $R^{15}$ or $R^{16}$ is an electron-withdrawing.

2. The compound according to claim 1, provided that when $R^4$ is an electron-donating group that contains a structure represented by the general formula (2), $R^{12}$ is a hydrogen atom:

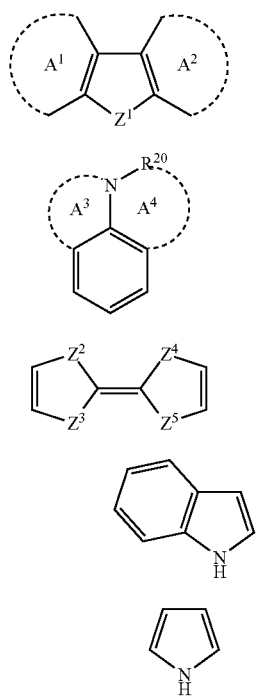

General Formula (2)

General Formula (3)

General Formula (4)

D4

D6 wherein, in the general formula (2), $Z^1$ represents an oxygen atom or a silicon atom, and may form, each independently at $A^1$ and $A^2$, an aromatic ring, a heteroaromatic ring, an aliphatic ring or a nonaromatic hetero ring.

3. An organic electroluminescence element having an anode, a cathode, and at least one organic layer containing a light-emitting layer between the anode and the cathode, wherein the light-emitting layer contains a host material, and a compound according to claim 1, which radiates delayed fluorescence.

4. In an organic electroluminescence display device comprising an organic electroluminescence element, wherein the improvement comprises the organic electroluminescence element is in accordance with claim 3.

5. The organic electroluminescence element according to claim 3 wherein $R^4$ and $R^{12}$ are both hydrogen.

6. The organic electroluminescent element of claim 5, wherein, in the general formula (1'), at least one of $R^2$ or $R^7$ is an electron-donating group.

7. The organic electroluminescent element of claim 3, wherein, in the general formula (1'), at least one of $R^{10}$ or $R^{15}$ is an electron-withdrawing group.

8. The organic electroluminescence element according to claim 3, wherein at least two of $R^1$, $R^2$, $R^3$, $R^4$, $R^5$, $R^6$, $R^7$ and $R^8$ in the general formula (1') each are an electron-donating group.

9. The organic electroluminescence element according to claim 3, wherein, in the general formula (1'), at least one of $R^1$, $R^2$, $R^3$ or $R^4$ is an electron-donating group, and at least one of $R^5$, $R^6$, $R^7$ or $R^8$ is an electron-donating group.

10. The organic electroluminescence element according to claim 3, wherein, in the general formula (1'), at least one of $R^2$ or $R^3$ is an electron-donating group, and at least one of $R^6$ or $R^7$ is an electron-donating group.

11. The organic electroluminescence element according to claim 3, wherein at least one of $R^1$, $R^2$, $R^3$, $R^4$, $R^5$, $R^6$, $R^7$ or $R^8$ is an electron-donating group other than D9 that contains a structure represented by any of the following general formulae (2) to (4):

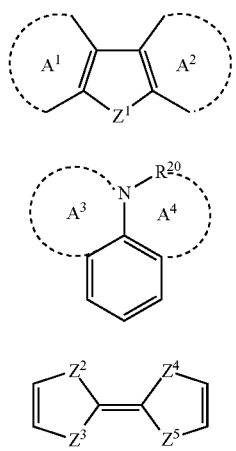

General Formual (2)

General Formula (3)

General Formula (4)

wherein, in the general formula (2), $Z^1$ represents a nitrogen atom, an oxygen atom, a sulfur atom or a silicon atom, and may form, each independently at $A^1$ and $A^2$, an aromatic ring, a heteroaromatic ring, an aliphatic ring or a nonaromatic hetero ring; in the general formula (3), $R^{20}$ represents a hydrogen atom, an aryl group or an atomic group necessary for forming the ring structure represented by $A^4$, and may form, each independently as $A^3$ and $A^4$, a heteroaromatic ring or a nonaromatic hetero ring; in the general formula (4), $Z^2$, $Z^3$, $Z^4$ and $Z^5$ each independently represent an oxygen atom or a sulfur atom.

12. The organic electroluminescence element according to claim 3, wherein at least one of $R^1$, $R^2$, $R^3$, $R^4$, $R^5$, $R^6$, $R^7$ or $R^8$ is an electron donating group that contains a structure of any of the following D1, D2, D3, D4, D5, D6, D7, D8, or D10:

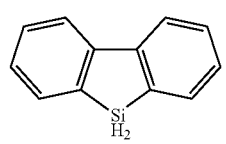

D1

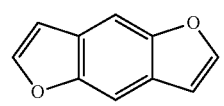

D2

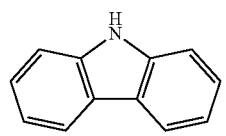

D3

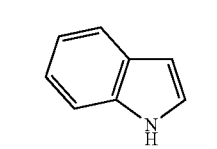

D4

-continued

D5 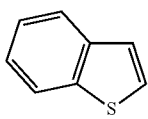

D6 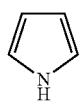

D7 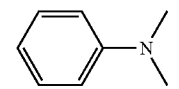

D8 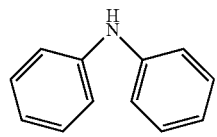

D10 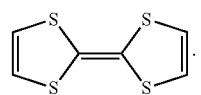

13. The organic electroluminescence element according to claim 12, wherein at least one of $R^1$, $R^2$, $R^3$, $R^4$, $R^5$, $R^6$, $R^7$ or $R^8$ is an electron-donating group that contains a structure represented by the above D3.

14. The organic electroluminescence element according to claim 3, wherein at least two of $R^9$, $R^{10}$, $R^{11}$, $R^2$, $R^{13}$, $R^{14}$, $R^{15}$ and $R^{16}$ in the general formula (1') each are an electron-withdrawing group.

15. The organic electroluminescence element according to claim 3, wherein, in the general formula (1'), at least one of $R^9$, $R^{10}$, $R^{11}$ or $R^{12}$ is an electron withdrawing group, and at least one of $R^{13}$, $R^{14}$, $R^{15}$ or $R^{16}$ is an electron-withdrawing group.

16. The organic electroluminescence element according to claim 3, wherein, in the general formula (1'), $R^{10}$ or $R^{11}$ is an electron-withdrawing group, and $R^{14}$ or $R^{15}$ is an electron-withdrawing group.

17. The organic electroluminescence element according to claim 3, wherein, in the general formula (1'), $R^{10}$ or $R^{11}$ is a cyano group, and $R^{14}$ or $R^{15}$ is a cyano group.

* * * * *